United States Patent [19]

Schwarz

[11] Patent Number: 5,741,895
[45] Date of Patent: Apr. 21, 1998

[54] IDENTIFICATION OF CELL DENSITY SIGNAL MOLECULE

[75] Inventor: Richard I. Schwarz, Oakland, Calif.

[73] Assignee: The Regents of the University of California, Oakland, Calif.

[21] Appl. No.: 445,367

[22] Filed: May 19, 1995

Related U.S. Application Data

[63] Continuation of Ser. No. 49,481, Apr. 19, 1993, abandoned, which is a continuation-in-part of Ser. No. 570,422, Aug. 21, 1990, abandoned.

[51] Int. Cl.$^6$ .............................. C07K 1/14; C07K 1/34; C07K 14/465; C07K 14/50
[52] U.S. Cl. .................. 530/399; 530/356; 530/414; 530/427; 530/840
[58] Field of Search .................................. 424/549, 582; 435/70.3; 514/8, 12, 21; 530/350, 351, 356, 397, 398, 399, 427, 840, 841, 850, 414

[56] References Cited

U.S. PATENT DOCUMENTS 4,731,357  3/1988  Franklin et al. .......................... 514/10

OTHER PUBLICATIONS

Harris et al. Protein Purification Methods. Oxford: IRL Press. 1989, pp. 9,10,57–60,62.

Martis et al. A Simple Fractionation of Chicken Egg Yolk . . . In Vitro Cellular & Developmental Biol. May 1986, vol. 22, No. 5, pp. 241–246.

Primary Examiner—Jeffrey E. Russel
Attorney, Agent, or Firm—Kathleen Dal Bon; Paul R. Martin

[57] ABSTRACT

Disclosed herein is a novel proteinaceous cell density signal molecule (CDS) between 25 and 35 kD, which is secreted by fibroblastic primary avian tendon cells in culture, and causes the cells to self-regulate their proliferation and the expression of differentiated function. It effects an increase of procollagen production in avian tendon cell cultures of ten fold while proliferation rates are decreased. CDS, and the antibodies which recognize them, are important for the development of diagnostics and treatments for injuries and diseases involving connective tissues, particularly tendon. Also disclosed are methods of production and use.

3 Claims, 2 Drawing Sheets

IDENTIFICATION OF CELL DENSITY SIGNAL MOLECULE

REFERENCE TO RELATED APPLICATION

This application is a Rule 60 continuation from U.S. patent application Ser. No. 08/049,481 filed Apr. 19, 1993, now abandoned, which is a Continuation-In-Part U.S. patent application Ser. No. 07/570,422, filed Aug. 21, 1990, now abandoned.

REFERENCE TO GOVERNMENT INTEREST

This invention was made in the course of contract DE-AC03-76SF0098 between the United States Department of Energy and the University of California for the operation of Lawrence Berkeley Laboratory. The United States Government has certain rights to this invention.

BACKGROUND OF THE INVENTION

1. Technical Field

This invention is related to therapeutics and the regulation of cellular growth and differentiated function. More specifically, it relates to cell density signal molecules produced by fibroblastic cells (for example, tendon cells), to the antibodies which recognize them, and to the use of these molecules in the treatment and repair of connective tissue injury disease, and regulation of cellular proliferation.

2. Description of Related Art

The level of collagen expression, a differentiated function of some fibroblastic cells in culture, is under the regulation of several environmental factors, one of which is cell density. Beginning in the early 1960's investigators observed that an enhancement of collagen production was dependent upon an increase in cell density; but, despite its long history, little is known about the signaling mechanism that allows the cell to recognize the presence of its neighbors and translate this information into increased collagen synthesis.

Most cell types which naturally express procollagen in vivo lose this ability over time when placed in cell cultures. However, primary avian tendon (PAT) cells, when grown in a cell culture environment that is permissive for high procollagen expression, retain the potential for high levels of collagen expression, and, in this regard, demonstrate a sensitivity to the density of the cell culture. PAT cells increase their production of procollagen, in direct relation to cell density, from less than 10% to about 50% of total protein synthesis. See for example, Schwarz, R. I. and M. J. Bissell, *Proc. Nat. Acad. Sci.* (1977) 74:4453–4457.

The proliferative capacity of cells in culture is also affected by cell density. However, a definitive correlation has been difficult to obtain because cell proliferation is affected by many cell culture parameters, only one of which is cell density.

For instance, it is difficult to distinguish the effect of density per se from the possibility that cell density changes are a subset of the nutritional needs of the cell. Similarly, decreased access to growth factors as cells lay down an extracellular matrix might explain the cell density effect. Changing the medium has been shown to be sufficient to stimulate cell division. Even just shaking the medium above the cells can stimulate cells to divide (Stoker, M. and D. Piggott, *Cell* (1974) 3: 207–215).

Cell contact may also play a role as demonstrated by the fact that membrane components, shed into the medium, act to inhibit cell proliferation.

Consequently, the relationship between cell density on the one hand and cell proliferation and the expression of differentiated function (procollagen gene expression in the case of PAT cells) on the other hand, has been a complex problem for which it has been particularly difficult to design definitive experiments.

Despite these complications, several publications describe proteins which are reported to affect density dependant cell growth. For example a 40–45 kD density-dependent growth inhibitor (designated IDF-45), isolated from mouse 3T3 cells has been described in Harel, L., et al., *J. Cell. Physiol.* (1984) 119:101–106; Harel, L., et al., *J. Cell. Physiol.* (1985) 123:139–143; and Blat, C., et al., *J. Cell. Physiol.* (1987) 130:416–419.

Lipkin, G., et al. (*Cancer Res.* (1978) 38:635–643), and Fass, E., et al. (*J. Invest. Dermitol.* (1986) 87:309–312) disclose a contact inhibitory factor, isolated from hamster melanocytic cells, which restores density-dependent growth to melanoma cells.

Yaoi, Y. and K. Motohashi (*GANN Monograph on Cancer Res.* (1980) 25:29–39) disclose a low molecular weight (6–8 kD) growth inhibitory factor from the cell surface of chick embryo fibroblasts.

The subject invention discloses a proteinaceous cell density signal molecule, exhibiting a molecular weight of at least about 25 kD to at most about 35 kD, most preferably about 30 kD, which: 1) first associates with the extracellular matrix of PAT cells in culture; 2) transiently stimulates the proliferation of these cells; and, 3) subsequently stimulates procollagen gene expression.

SUMMARY OF THE INVENTION

A proteinaceous cell density signal (CDS) molecule has now been found. The CDS is capable of temporarily stimulating the proliferation of fibroblastic cells in culture and thereafter promoting differentiated gene expression. The CDS is secreted by fibroblastic cells, for example, tendon cells, and can be obtained free of such cells. If desired, it can be substantially purified.

This novel polypeptide is secreted by fibroblastic cells, such as tendon cells, and provides a means by which the cells self-regulate their proliferation and the expression of differentiated function. The CDS, and the antibodies which recognize it, are important for the development of diagnostics and treatments for injuries and diseases involving connective tissues, particularly tendon.

More particularly, naturally occurring avian CDS is a 25 kD to 35 kD growth stimulatory polypeptide, expressed by primary avian (chicken) tendon cells in culture, which is believed to quickly bind to the extracellular matrix (ECM) produced by these cells. This quick binding is believed to restrict the diffusion of CDS and thereby proximally limit the proliferative effect of this molecule.

At some time after the binding of CDS to the ECM, a subsequent event—which is not presently understood—occurs such that the activity of CDS is altered and it becomes stimulatory for the expression of procollagen, a differentiated function of the avian tendon cells.

CDS may be harvested from cultures of tendon cells by gentle agitation. This treatment removes a substantial fraction of CDS from the cell layer and cells which have been so treated, exhibit reduced expression of procollagen. CDS, so harvested, exhibits growth stimulatory activity when added back to cultures of quiescent tendon cells. This surprising and unique characteristic of CDS—that both its removal from and addition to cultures of tendon cells is growth stimulatory—is a feature which distinguishes this polypeptide.

The harvested CDS described above is found in the medium as a multi-molecular complex with an apparent molecular size of at least greater than 30 kD, more usually greater than 60 kD, and most usually approximately 100 kD. After treatment with a sulfhydryl bond disrupting agent, such as DTT, a monomeric, approximately 30 kD, CDS molecule can be identified.

One aspect of the invention is directed to isolated, purified, naturally occurring CDS, and fragments, mutations and modifications thereof which retain CDS biological characteristics.

Another aspect of the invention are antibodies which are specific for CDS.

Still another aspect of the invention are methods of obtaining, isolating and purifying CDS.

Yet another aspect of the invention are methods of using CDS for the therapeutic treatment of injuries to, and diseases of, connective tissue, especially tendon.

DETAILED DESCRIPTION OF THE INVENTION

I. Definitions

Figure 1:
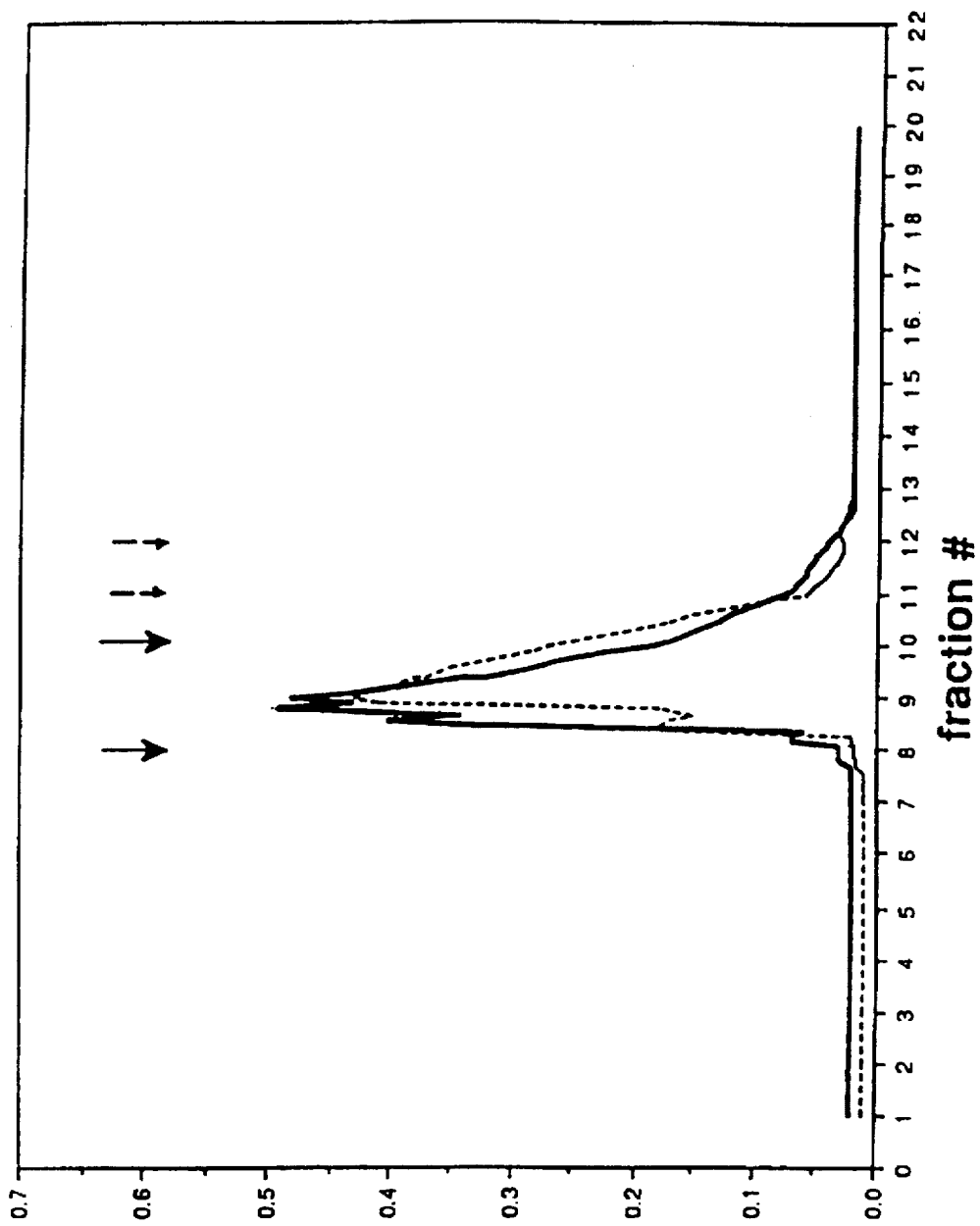
FIG. 1 is a graph showing the chromatographic separation of proteins isolated from primary avian tendon cells. The continuous arrows mark the range of CDS activity prior to DTT treatment and the dashed arrows mark the range of activity after DTT reduction.

"Autogenic" means derived either from the same B individual; from a cell culture derived from an individual; from multiple inbred individuals; or from cultures derived from multiple inbred individuals.

"Differentiated gene expression" or the expression of "differentiated function" is the transcription and translation of structural genes other than those associated with cellular division or viability. The polypeptides so expressed are those which characterize differentiated cells as opposed to immature or "blastic" cells.

The "extracellular matrix" (ECM) refers to a network of macromolecules upon, or within, which cells subsist. The extracellular matrix is comprised of, but not limited to, collagen, laminin, fibronectin, glycosaminoglycans, proteoglycans, etc. In vivo, the ECM is produced by cells within the matrix or by peripheral cells, and is an integral part of stromal tissue. In culture, many cell types require an ECM for the expression of proper differentiated characteristics.

Proteinaceous molecules which are "functionally homologous" exhibit the same functional characteristics. For example, an enzyme from one species is functionally homologous with an enzyme from another species if they both catalyze the same reaction. Thus, proteinaceous CDS molecules from different species would be functionally homologous if they exhibited the same amphipathic regulation of growth and differentiated function for the corresponding autogenic fibroblastic cells in culture.

A "polypeptide" includes the naturally occurring polypeptide and all fragments, deletions, additions, substitutions, mutations and modifications of the natural polypeptide which retain the biological activities of the naturally occurring polypeptide. A glycosylated or otherwise modified polypeptide is included within the scope of the term as used herein and may also be more specifically referred to as a proteoglycan, glycopeptide or glycoprotein. A proteinaceous molecule comprises a polypeptide.

A "primary culture of cells" is derived from in vivo tissue and not passaged. Primary cultures can be distinguished from cell strains and established cultures principally by the retention of a karyotype which is substantially identical to the karyotype found in the tissue from which the culture was derived, and by the cellular responses to manipulations of the environment, responses which are substantially similar to the in vivo response.

"Unsupplemented basal growth medium" is a defined cell culture growth medium without the addition of serum or other growth supplements.

II. Modes for Carrying Out the Invention

Normal cells in culture are known to respond to cell density by altering their proliferation rates and their pattern of protein expression. Primary avian tendon (PAT) cells, derived from chick embryos, are a case in point in that, at high cell density, procollagen production increases about 10-fold while proliferation rates approach zero. In the subject application, the signaling mechanism for both proliferation and procollagen expression is shown to have the characteristics of a loosely—bound proteinaceous molecule exhibiting an SDS gel migration size of about 25 kD to about 35 kD.

This molecule, termed the cell density signal (CDS) is produced by fibroblastic cells and can be isolated from the media of cultures of such cells. Thus, in general terms, the CDS molecule can be obtained by the process of:

a) preparing fibroblastic cultures of cells, including tendon cells, derived from animals such as avian or mammalian and including embryonic cells derived from such sources;

b) maintaining the cultures in a tissue culture medium such as F-12 under appropriate environmental conditions for growth, such as 37°–42° C., high humidity, medium supplementation with ascorbate and serum, and elevated $CO_2$ levels, for from 1 to 5 days in order to provide high cell density in the primary culture;

c) removing the cell growth medium from the cultured cells and replacing it with a medium suitable for maintaining cells at high density;

d) agitating the cultured cells and added medium over a period of at least one day and preferably 2 to 6 days in order to facilitate release of CDS from the cells into the medium;

e) separating the medium and released CDS from the cells;

f) concentrating the CDS and other proteins in the medium such as by precipitation and centrifugation, gel filtration, membrane ultrafiltration, and the like;

g) fractionating the CDS and other proteins to remove low molecular weight contaminants and retain the CDS in a high molecular weight complexed form which is retained by a 30 kD exclusion filter;

h) treating the retained complex with a reducing agent to liberate the CDS as a 25–35 kD material; and i) isolating the CDS as the 25–35 kD material such as by passing it through a nominal 30 kD filter or the like.

The CDS so isolated is comprised of a polypeptide, and is defined by its size—about 25–35 kD, and especially about 30 kD as measured by a SDS-PAGE comparison with known proteinaceous standards. It is also characterized by its biological activity—the ability to initially stimulate the proliferation of embryonic tendon cells in culture and thereafter promote the expression of a differentiated function, namely procollagen gene expression. It is further characterized by its heat stability at 90° C., its stability with regard to pH and DTT, and trypsin treatment, its Tris ion instability, and sensitivity to pronase and proteinase K.

After secretion by cells in culture, CDS becomes associated with the extracellular matrix. However, as described above, it may be displaced from the ECM into the culture medium by agitation of the cell culture. This action stimulates cellular proliferation only under conditions were there was a high medium-to-cell ratio (presumably because under this condition reassociation is minimized). In contrast, under conditions where there was sufficient cells to contribute a high concentration of CDS to the medium, agitation had little effect, presumably because of high frequency reassociation. This suggests that CDS acts as a growth inhibitor.

On the other hand, the activity of medium which has been conditioned by agitation over confluent cultures was stimulatory when added to a population of cells with a high medium-to-cell ratio. Moreover, PAT cells would not grow out into an area devoid of other cells but would divide to fill an area of moderate cell density. These observations lead to the opposite conclusion that the CDS is a growth stimulator. Using the growth promoting activity of the conditioned medium as a basis for selection, the CDS was shown to have unique physical characteristics. The polypeptide is heat, pH, and DTT stable (retention of greater than 75% of original activity) but is sensitive to inactivation by Tris ion (less than 40% of original activity). CDS is resistant to inactivation by trypsin, but is sensitive to pronase and proteinase K. By gel exclusion chromatography it is larger than 100 kD; but after DTT treatment its mobility shifts to approximately 30 kD while retaining its biological activity. Overnight labeling followed by a simple fractionation relying on this mobility shift resulted in a single radiolabeled band, corresponding to a molecular weight of approximately 30 kD when subjected to SDS-poly acrylamide gel electrophoresis SDS gel analysis).

The fact that adding CDS or removing it (continuous agitation into a large volume of medium) gives the same growth stimulatory cellular response, is believed to be due to the fact that the CDS has different activities depending on its presentation to the cell. CDS in conditioned medium is an aggregate that can bind to the cell matrix and, in this form, acts as a growth stimulator. However, once bound in the extracellular matrix, CDS may form a complex with itself or with a heretofore unknown factor, such that it then acts as a growth inhibitor and inducer of procollagen production.

A. Growth of Primary Avian Tendon Cells in Culture

PAT cells were isolated from 16 day chick embryos by a modification of the method of Dehm, P. and D. J. Prockop (*Biochem. Biophys. Acta.* (1971) 240:358–369), herein incorporated by reference. Unless otherwise specified, cells were seeded onto 25 cm$^2$ tissue culture flasks and grown in F12 medium supplemented with 0.2% fetal bovine serum and 50 µg/ml ascorbate (Schwarz et al., 1979).

When a large medium-to-cell ratio was required, cells ($10^4$) in medium without serum were seeded inside a glass cloning ring (6 mm inside diameter) that was placed within a standard tissue culture plate (60 mm diameter). Medium was placed on the outside of the cloning ring to equalize hydrostatic pressure. After 1 h, when the cells had attached, the cloning ring was removed. The medium was changed to F12 medium (5 ml) supplemented with 0.2% fetal bovine serum (Gibco) and 50 µ/ml ascorbate. Under these conditions it was found that the cultures performed slightly better at a higher $CO_2$ concentration (3×bicarbonate, 15% $CO_2$). Consequently, all cells were grown at the higher concentration. Cells grown at normal medium to cell ratios were not affected by the higher $CO_2$ concentration.

B. CDS Purification

Growth medium with 0.2% serum was replaced with basal medium (6 ml of F12 for 150 cm$^2$ flask) on high cell density cultures and this was shaken gently (60 rpm on a rotary shaker) at about 39° C. for 1 h. This was done twice a day for 4 days. The cell-free conditioned medium was stored at 4° C. (it is stable for months).

Ammonium sulfate was added to make a 40% to 60%, preferably a 50% saturated solution (4° C.) and left overnight. This was spun at approximately 35,000 rpm for 30 min (45Ti rotor, Beckman). The pellet was resuspended in phosphate buffered saline (PBS) and concentrated by ultrafiltration (30 kD exclusion filter, CX-30; Millipore). This was diluted again and reconcentrated to further reduce the ammonium ion concentration which is toxic to cells. The final concentration was adjusted to a concentration of 100 X when compared to the original medium volume. Dilution to 1X concentration gave approximately equal growth stimulating activity as the original conditioned medium.

The concentrate was treated with 10 mM DTT (dithiothreitol) for 30 minutes at 37° C. This was again passed through a 30 kD ultrafilter (PF-30, Millipore). The ultrafiltrate retained about half the biological activity as the original medium.

To label CDS, cells (25 cm$^2$ flask, 5 ml) were labeled with 1 mCi of radioactive amino acid in growth medium overnight. The labeled medium was removed and basal medium (1 ml) was added and this was conditioned by shaking (as above). The ammonium precipitation step was not required and the medium was concentrated and diluted B with PBS several times to reduce the levels of unincorporated label. Finally, this was concentrated to 100 µl and treated with DTT as above. After 30 kD ultrafiltration both the filtrate and retentate were applied to an SDS PAGE gel (3% stacking, 15% resolving). The gel was impregnated with Enhance (NEN) and exposed to X-ray film at −70° C.

C. Assessment of Procollagen Gene Expression

In situ hybridization is often used as a method for distinguishing certain cells in a mixed population based on the presence of a specific mRNA. This technique can be used quantitatively to demonstrate the effect of cell density changes on the amount of procollagen mRNA in individual cells. This technique allows for the most direct and least ambiguous measurement of the relation between cell density and differentiated gene expression for PAT cells, procollagen expression.

PAT cells were fixed with 4% paraformaldehyde in PBS (10 min) followed by washing in 0.1M glycine in PBS. After fixation, the cells were covered with 2 ml of hybridization solution (60% deionized formamide, 0.1M PIPES p H 6.4, 0.4M NACl, 5% poly A RNA [2.5 mg/ml]). After prehybridization for several hours at 55° C., the hybridization solution was changed, labeled probe was added, and the cells were hybridized for 48 h. Unless otherwise stated, $2\times10^6$ cpm of labeled probe was used with a specific activity of $3.3\times10^7$ cpm/ µg.

After hybridization, the cells were washed twice for 1 h in 0.1% Triton X-100 in 2×SSC at 55° C. and then twice for 1 h in 0.1% Triton X-100 in 0.1×SSC at 60° C. The cells were dehydrated with graded alcohol washes and then covered with photographic emulsion (NBT2, Kodak). Development times varied depending on the specific activity of the probe. With the standard specific activity stated above, the exposure time was 2 weeks. Several early experiments used a 2-fold higher specific activity probe (by labeling with both $^3$H-ATP and $^3$H-UTP) and exposure time was correspondingly shortened to 1 week. The cells were stained with Wrights.

In experiments quantifying the amount of $^3$H-RNA probe hybridized, the cell layer was solubilized using 1% SDS and the level of radioactivity measured by scintillation counting.

Fixed cells were treated in the same manner as in dot-blot hybridization (a procedure known to those skilled in the art): the volume of hybridizations solution was on the order of mls; no pretreatments other than prehybridization were used; and only salt and detergent solutions were used in the post-hybridization washes.

Using dot-blot hybridization techniques on extracted mRNA, it had been previously shown by Rowe, L. B. and R. I. Schwarz, (Mol. and Cell. Biol. (1983) 3:241-249) that ascorbate treatment can increase procollagen mRNA production about 5 fold in PAT cell cultures. Using an in situ dot blot technique for ascorbate induced and uninduced cells, the same ≈5 fold increase was observed for RNA.

The kinetics of the reaction was much slower than others have reported, being about two orders of magnitude slower than an equivalent dot hybridization, but followed an exponentially decreasing function indicative of a pseudo first order reaction. In the case of ascorbate induced cells, background levels of a nonhomologous probe with an equal number of counts started (1.5 h) at 13% and ended (42 h) at 3% of the specific signal. The large solution volumes and the lack of dehydration of the cells prior to hybridization probably account for the slower kinetics under these conditions by slowing entry of the probe into the cell. This difference did not appear to be due to probe size in that probes of different sizes (0.2 to 2 kB) hybridized equally well to PAT cells. The data are consistent with the rate-limiting step in the in situ hybridization reaction being entry of the probe into the cell through a limited number of ports.

Most importantly, by using conditions of relatively high probe concentrations with long incubation times, the amount of probe hybridized in situ reflects the level of mRNA in the cell. In the examples described below, detection was by autoradiography and the relative concentration of procollagen mRNA was reflected in the exposed silver grain densities over individual cells and this varied by an order of magnitude with cell density.

This technique is much more specific, accurate and sensitive than techniques previously utilized to measure effects in culture on procollagen gene expression. Furthermore, it allows for the observation of different effects of different cell densities on the same culture dish.

D. Sequencing of CDS

Purified CDS, recovered and isolated from the ultrafiltration filtrate, is sequenced by subjecting up to 100 pmoles (estimated from staining intensity on acrylamide gels) to automated Edman degradation utilizing an Applied Biosystems 477A pulsed liquid phase protein sequenator.

N-terminal sequencing may not be adequate to support efforts to clone the cDNAs of the CDS. For instance, the CDS may be blocked or modified at the N-terminal or alternatively, the N-terminal sequences may not show favorable regions for generation of oligonucleotide probes. In such case, the CDS is digested with a protease (e.g., V8—See Harlow, E. & Lane, D. Antibodies A Laboratory Manual, Cold Spring Harbor Press, 1989) and the peptide fragments are purified in order to generate additional sequence information. In such cases the protein is concentrated to a 5 µL volume by vacuum centrifugation, and is then digested. Protease fragments are purified for sequencing by reverse phase HPLC using a Brownlee RP 18 narrow bore column and an Applied Biosystems 130A liquid chromatograph—designed specifically for purification of mole samples.

Sequence data thus obtained are compared to known protein sequences by computerized searches of the Protein Identification Resource of the NB RF, and of the Swiss protein database, in order to determine their novelty or relationship to other protein sequences.

E. Screening of cDNA Libraries and the Molecular Cloning of CDS Encoding DNA

Primary avian tendon cell cultures can be used to prepare a cDNA library which is then screened for particular DNA sequences that encode CDS specific polypeptides. Techniques for the preparation of a cDNA library are commonly used, described in laboratory manuals and known to those skilled in the art. The preparation of these cDNA libraries is described in detail in Maniatis, T. et al, Molecular Cloning, (1982) CSHL Press. A convenient approach is the insertion of cDNA fragments into a lambda phage vector e.g. lambda gt10 or lambda gt11 as described by Maniatis, supra.

Methods of screening cDNA libraries are also well known to those skilled in the art. The amino acid sequence of the CDS is analyzed utilizing programs from DNAstar (Madison Wis.) in order to identify optimal regions for construction of oligonucleotide probes. Redundant oligonucleotide probes are synthesized with a DNA synthesizer (380A: Applied Biosystems Inc. Foster City Calif.) by the phosphoramidite method. Oligonucleotides are purified on Sephadex G-50 columns and stored at −20° C. The redundant probes are 5'-labeled with τ-[32P]ATP (E.I. du Pont de Nemours & Co., inc., Boston, Mass.) using T4 polynucleotide kinase. Libraries are screened using up to $10^6$ individual plaques per library, with the redundant oligonucleotide probes. Duplicate nylon membranes containing phage are prepared and prehybridized in 5×SSPE (0.9M NaCl, 50 mM $NH_2PO_4$, 5 mM EDTA, pH7.4), 0.2% SDS, and 0.005% denatured salmon sperm DNA for 2 hours at 50° C. with 8 filters per 50 ml prehybridization fluid per bag. Membranes are hybridized with approximately 1 ng of labeled probe per ml, in fresh hybridization fluid, overnight at the appropriate temperature for the redundant probe mixture. Membranes are then washed at room temperature for 45 minutes in 1 liter of 5×SSPE per 40 filters, followed by a 1 minute wash in fresh buffer at 50° C., slightly air-dried, and exposed to Kodak XAR-5 film, with intensifying screens, for 72 hours at −70° C.

After analysis, filters are stripped of hybridized label by incubation in 5×SSPE at 70° C. for 10 minutes and subsequently hybridized with a second probe under the same conditions. This procedure is repeated for each probe. Recombinant clones which hybridize with probes will be selected from the library and plaque purified.

Recombinant phage DNA is then purified and digested with an appropriate restriction endonuclease to yield the amplified cDNA insert. Inserts are then ligated into M13 mp series phage and sequenced using the "dideoxy" method described by Sanger (Biggin, M. D. et al, Proc Nat Acad Sci (1983) 80:3963). Depending on the size of the cDNA, it may be necessary to restrict the clone, and subclone the fragments into M13. If the cDNA clones are not complete, a repeat screen of the library with the partial cDNA would be required.

The complete sequence of the CDS cDNA is then compared against known sequences in the GenBank database. DNAstar is used for nucleotide and polypeptide analyses and sequence comparisons.

Selected cDNA inserts which encode CDS can then be incorporated into an expression system. The cDNA is operably linked to heterologous control sequences to form an expression vector. The control sequences are chosen to be functionally compatible with the recombinant host cell into which the expression vector is introduced. These procedures are known to those skilled in the art and described in Maniatis, supra.

Expression can be in procaryotic or eucaryotic systems. Procaryotes most frequently are represented by various strains of E. coli. However, other microbial strains may also be used, such as bacilli (e.g. Bacillus subtills), various species of Pseudomonas, or other bacterial strains. In such procaryotic systems, plasmid vectors which contain replication sites and control sequences derived from a species compatible with the host are used. For example, E. coli is typically transformed using derivatives of pBR322, a plasmid derived from an E. coli species by Bolivar et al., Gene (1977) 2:95. Commonly used procaryotic control sequences, which are defined herein to include operons with promoters for transcriptional initiation, optionally with an operator, along with ribosome binding site sequences, include such commonly used promoters as the beta-lactamase (penicillinase) promoter, lactose (lac) promoter systems (Chang et al., Nature (1977) 198:1056), the tryptophan (trp) promoter system (Goeddel et al., Nucleic Acids Res (1980) 8 :4057), the lambda-derived PL promoter and N-gene ribosome binding site (Shimatake et al., Nature (1981) 292:128). Any available promoter system compatible with procaryotes can be used.

The expression systems useful in eucaryotic hosts comprise promoters derived from appropriate eucaryotic genes. A class of promoters useful in yeast, for example, includes promoters for synthesis of glycolytic enzymes, including those for 3phosphoglycerate kinase (Hitzeman et al., J Biol Chem (1980) 255:207). Other promoters include those from the enolase gene (Holland, M. J., et al. J Biol Chem (1981) 256:1385) or the Leu2 gene obtained from YEp13 (Broach, J., et al., Gene (1978) 8:121).

Suitable mammalian promoters include metallothionein, the early and late promoters from SV40 (Fiers et al., Nature (1978) 273:113), or other viral promoters such as those derived from polyoma, adenovirus II, bovine papilloma virus or retroviruses. Suitable viral and mammalian enhancers may also be used. In the event plant cells are used as an expression system, the nopaline synthesis promoter is appropriate (Depicker, A., et al., J Mol Appl Gen (1982) 1:561).

The expression system is constructed from the foregoing control elements which are operably linked to the CDS sequences by employing standard ligation and restriction techniques which are well understood in the art. Isolated plasmids, DNA sequences, or synthesized oligonucleotides are cleaved, tailored, and religated in the forms desired.

Other systems for expression of CDS encoding cDNA include insect cells and vectors suitable for use in these cells. These systems are known in the art, and include, for example, insect expression transfer vectors derived from the baculovirus Autographa californica nuclear polyhedrosis virus (AcNPV), which is a helper-independent, viral expression vector. Expression vectors derived form this system usually use the strong viral polyhedrin gene promoter to drive expression of heterologous genes. Currently the most commonly used transfer vector for introducing foreign genes into AcNPV is pAc373. Many other vectors, know to those of skill in the art, have also been designed for improved expression. These include, for example, pVL985 (See Luckow and Summers (1989)).

Methods for the introduction of heterologous DNA into the desired site in the baculovirus virus are known in the art. (See Summer and Smith, Texas Agricultural Experiment Station Bulletin No. 1555; Ju et al. (1987); Smith et al. (1983); and Luckow and Summers (1989)). For example, the insertion can be into a gene such as the polyhedrin gene, by homologous recombination; insertion can also be into a restriction enzyme site engineered into the desired baculovirus gene. The inserted sequences may be those which encode all or varying segments of the polyprotein.

The signals for posttranslational modifications, such as signal peptide cleavage, proteolytic cleavage, and phosphorylation, appear to be recognized by insect cells. The signals required for secretion and nuclear accumulation also appear to be conserved between the invertebrate cells and vertebrate cells. Examples of the signal sequences from vertebrate cells which are effective in invertebrate cells are known in the art, for example, the human interleukin-2 signal ($IL2_s$) which is a signal for transport out of the cell, is recognized and properly removed in insect cells.

F. Analysis of Mammalian Genomic Sequences of CDS DNA

CDS-encoding genes are obtained from genomic libraries of chickens (available from Clontech, Palo Alto, Calif.) or various mammals (generally available, in phage, from the ATCC or commercial sources). For example, a human genomic library of fetal liver cells in Charon 4A phage is available (ATCC 37333). The library contains $10^6$ independent recombinants with an insert size of 15–20 kb and it is screened with cDNA essentially as previously described.

Phages are sequentially adsorbed onto duplicate 8×8 cm nylon membrane filters. Filters are prehybridized in 5×SSPE, 50% formamide, 5×Denhardt's solution, 0.5% SDS and 0.005% denatured salmon sperm DNA for 2 hours at 42° C. with 8 filters per 50 ml of prehybridization fluid. Filters are hybridized with approximately 1.0 ng of labeled avian CDS cDNA per ml of fresh prehybridization fluid, containing 10% dextran sulphate and 2×Denhardt's solution, overnight at 42° C.

The stringency of the hybridization solution can be adjusted to account for the non-homology between the avian and mammalian CDS polypeptide. Stringency can be lowered to increase the tolerance for mismatch in the hybridization by raising the salt concentration and/or lowering the temperature of the hybridization. The degree of non-homology will vary within different regions of functionally homologous polypeptides. Generally, the sites of functionally homologous activity will demonstrate the greatest degree of homology. These sites are predictable based on analyses of the structure of the avian CDS polypeptide. Several probes coding for various regions of the CDS polypeptide will be used to optimize locating regions of high conservation.

Avian CDS cDNA is labeled with $\alpha^{32}p$ dCTP and purified by Sephadex G-50 chromatography. Filters are then washed twice at room temperature for 15 minutes in 1 liter 2×SSPE and 0.2% SDS per 40 filters, followed by two 15 minute 50° C. washes in 0.1×SSPE and 0.2% SDS, slightly air-dried,and exposed to Kodak XAR-5 film, with intensifying screens, for 48 hours at −70° C.

Positive clones are selected from the library and plaque purified. Various probes derived from the cDNA are utilized to determine whether or not a complete copy of the gene is contained within the genomic clone. Recombinant phage DNA is next extracted, purified, and subjected to restriction digestion—all processes which are well known to those skilled in the art. Southern blots of the restriction fragments are hybridized with CDS cDNA to identify fragments containing the CDS gene. These fragments are then isolated and sequenced. From this information a restriction map is constructed and the introns of the gene are identified.

G. Preparation of Antibodies to CDS

Two approaches are utilized to raise antibodies to CDS and both approaches can be used to generate either polyclonal or monoclonal antibodies. In one approach, purified denatured CDS is obtained in quantities up to 75 µg and used to immunize mice using standard protocols; about 25 µg is adequate for immunization. For screening hybridomas, denatured CDS, which is soluble in 0.1% TFA and acetonitrile, can be radioiodinated and used to screen murine B-cell hybridomas for those which produce antibody. This procedure requires only small quantities of CDS such that 20 µg would be sufficient for labeling and screening of several thousand clones.

In the second approach, the amino acid sequence of CDS, as deduced from the gene, is analyzed to determine regions of high immunogenicity. The corresponding polypeptides are synthesized and are used in suitable immunization protocols to raise antibodies. Analysis to select appropriate epitopes is described by, for example, Ausubel, F. M. et al (*Current Protocols in Molecular Biology*, John Wiley & Sons, Vol. 2, Sec. IV, pp11.14.1, 1989). The optimal selections are usually the C-terminus, the N-terminus and internal regions of the polypeptide which are likely to be exposed to the external environment when the molecule is in its natural conformation (this determination is based on the hydrophilicity of the sites). Typically, selected peptides, about 15 residues in length, are synthesized using an Applied Biosystems Peptide Synthesizer Model 431A using fmoc-chemistry and coupled to keyhole limpet hemocyanin (KLH; Sigma) by reaction with m-maleimidobenzoyl-N-hydroxysuccinimide ester (MBS) (See Ausubel et. al, supra at pp 11.15.1). A cysteine is introduced at the N-terminus of the peptide to permit coupling to KLH. Rabbits are immunized with the peptide-KLH complex in complete Freund's adjuvant and the resulting antisera tested for antipeptide activity, for example, by binding the peptide to plastic, blocking with 0.1% BSA, reacting with antisera, washing and reacting with radioiodinated affinity purified specific goat antirabbit IgG.

Hybridomas may be also be prepared and screened using standard techniques. Hybrids are screened using radioiodinated CDS to identify those producing monoclonal antibody. In a typical protocol, prongs of plates (FAST, Becton-Dickinson, Palo Alto, Calif.), are coated with affinity purified specific rabbit-antimouse (or suitable anti species Ig) antibodies at 10 µg/ml. The coated prongs are blocked with 0.1% BSA, washed and exposed to supernatants from hybridomas. After incubation the prongs are exposed to radiolabeled protein, 1 ng/ml. Clones producing antibodies will bind a quantity of radioactivity which is detectable above background. Such clones are expanded and subjected to 2 cycles of cloning at 0.3 cell/well. Cloned hybridomas are injected into pristine treated mice to produce ascites, and monoclonal antibody is purified from the ascitic fluid by affinity chromatography on protein A.

EXAMPLES

Example 1
Growth Characteristics of PAT cells in Culture

PAT cells adapt quickly to the cell culture environment, and as primary cultures, display the normal phenotype expected for fibroblasts in culture. PAT cells show two common cell density effects on cell proliferation: a minimum requirement for cell density in order to grow, and an inhibition of growth at higher cell densities.

Both these cell density responses can be observed at the same time by establishing a cell density gradient within a PAT cell culture. This was done by seeding cells initially in a cloning ring (6 mm diameter in a 60 mm dish) and then removing the ring after the cells had attached. A benefit of this approach was that the medium to cell ratio was large (thus minimizing conditioning effects) while at the same time a cell density gradient was created within the dish.

PAT cells showed a unique response to this situation. They showed a limited ability to grow out into an area devoid of cells—only expanding the initial area from a diameter of 6 mm to 7 mm. In contrast, the cells within the initially seeded area grew rapidly until confluent. At this point the cells at the low cell density edge began to die. This was evident by the rounded-up morphology of the cells, and was also confirmed by trypan blue staining.

This effect was not due to a toxicity in the medium. If a cell scraper was used to remove one half of the circle of cells, the cells at the new edge would grow out and form a new low density edge even while the cells remaining at the original edge were dying. Similarly, if only a narrow groove was removed from the circle of cells, the cells were capable of filling in the groove except at the juncture of the old and new edge. This point of lowest cell density had a distinct indentation towards the center of the circle. This demonstrated that PAT cells can condition a localized microenvironment within a cell culture for growth so long as a minimum density of cells is present.

Example 2
Effect of Cell Density on Procollagen Gene Expression

Previously, the insensitivity of the assays employed required that an average value from over $10^5$ cells be used to analyze cell density changes in the collagen pathway. With an in situ hybridization assay for procollagen mRNA levels, cell density effects can be analyzed on a cell by cell basis and the effect of different cell densities within the same culture can be observed.

PAT cells were initially seeded inside a 6 mm diameter cloning ring placed in the middle of a standard 60 mm tissue culture dish as described in Example 1; After 1 h, when the cells had attached to the dish, the cloning ring was removed. The cells were cultured for 5 days by which time they had become confluent in the middle of the original ring. PAT cells showed only limited ability to grow out into the space at the edge of the ring devoid of cells, so that by the end of the 5 days, the circle of cells had only expanded to 7 mm. This expansion was sufficient to establish a low cell density edge while cells in the middle of the circle were at high cell density.

The cell density distribution caused a wide variation in procollagen mRNA levels. Those cells at a confluent density in the center of the ring contained high levels of procollagen mRNA as evidenced by the large numbers of exposed silver grains over them. In contrast cells at the low density edge had low levels of procollagen mRNA. Very similar results were obtained when the cell density gradient was created by seeding cells into a tilted tissue culture flask.

In those experiments where the cells were initially restricted by cloning rings there was a very high ratio of medium volume to cell number yet the cells remained responsive to cell density. This would be incompatible with simple models where the CDS acts as a stable factor that accumulates in the medium and where the CDS is thought to be readily diffusible because the effect of the CDS would have been diluted out.

Example 3
Confluent Cells Express Differentiated Function but Retain Capacity for Cell Division Despite the morphological uniformity of PAT cell cultures, it is possible that cells which are found at the periphery of a confluent cluster are a unique subset of the population. In this case, part of the gradient of procollagen expression described above might result from the selection of a proliferative cell type that produces lower amounts of procollagen.

To test this, PAT cells were initially seeded in cloning rings as described above and allowed to grow into a confluent circle of cells. The edge of a cell scraper was used to remove two 1.7 mm perpendicular swaths through the circular area of cells (~6 mm) forming a cross. This distance was small enough that the cells growing out from both sides met in the middle and would completely fill the gap. In situ hybridization showed that the cells that were part of the migrating front produced high levels of procollagen as the cell density increased. In contrast, when half of the circle of cells was scraped away, PAT cells migrating out into an empty space showed low levels of procollagen expression at the low cell density edge.

Thus, changes in procollagen mRNA levels in individual cells at the growing front are not due to cell selection but due to the cell density effect.

Example 4
CDS Accumulates in the Cell Layer

The fact that the CDS is not altered by medium volume suggests that the signal molecule accumulates in the cell layer, possibly in the extracellular matrix (ECM). One prediction of this hypothesis is that once the signal accumulates, its concentration in the cell layer or in the ECM should be independent of the continued presence of cells.

One test of this concept is to scrape away a portion of a cell cluster, but in such a way as to inhibit cell migration into an area in which the ECM has been removed.

To accomplish this, cells were initially plated in cloning rings and allowed to grow into confluent circles. Half the circle of cells were then scraped away with a scalpel blade. This roughened the surface of the plastic dish and prevented the cells from migrating out. After 48 h (a little over two half-lives for procollagen mRNA), the cells retained high procollagen mRNA levels at the roughened edge. The roughened edge itself did not stimulate procollagen mRNA synthesis as evidenced by the fact that cells located at the junction of the roughened edge and the natural edge of the circle (where procollagen mRNA synthesis has been shown to be low) showed very low levels of procollagen mRNA synthesis.

Cells at the scraped edge continued to maintain high levels of procollagen mRNA even though only half as many cells were in their immediate vicinity. This is consistent with a factor being bound to the ECM.

Example 5
Gentle Agitation Removes the CDS from the ECM

That the CDS is a loosely bound component of the ECM can be demonstrated by agitating the medium above the PAT cell monolayer and monitoring the effects on collagen expression and cellular proliferation. Others have demonstrated that growth factors can be influenced by the laminar flow of the medium over cells in culture (Dunn, G. A. & G. W. Ireland, *Nature* (1984)312:63–65).

In observing the effects on collagen expression, two conditions were used: one where cells were seeded initially in a cloning ring and the second where the cells were seeded evenly over the whole plate. The essential difference between these two conditions is in the ratio of medium volume to cell number. The cell cultures were grown at 39° C. until confluent and then placed on a rocking platform for two days (control plates were left unshaken).

The effect of agitation was dependent on the ratio of medium to cells. In the case of cells seeded evenly over the plate, shaking confluent cultures had no effect. In contrast, with cells initially seeded in cloning rings, shaking confluent cultures caused the level of procollagen mRNA to diminish and become independent of cell density.

This is consistent with a model whereby the CDS is a loosely bound component of the extracellular environment of the cell, and shaking releases the CDS into a large volume of medium, essentially removing it from the cells by dilution, and inhibiting the expression of procollagen mRNA. On the other hand, shaking confluent dishes into a relatively small volume of medium would prevent dilution of the CDS (about 2 orders of magnitude change in the ratio), resulting in a high level of reassociation of CDS with the cell layer, and little or no cellular effect.

These experiments where repeated but rather than looking for the effect of medium to cell ratio on procollagen synthesis, cells were assayed for proliferation using a pulse of $^3$H-thymidine, a technique of measuring growth known to those skilled in the art. A similar result was obtained. In the case of cells seeded in cloning rings and shaken for 24 hours, there was a dramatic increase in the number of labeled nuclei both at the edge and at the confluent center. In sharp contrast, culture dishes that had been evenly seeded showed little effect from shaking the medium.

In the unshaken condition, a cell at a confluent density is unaware of whether this cell density exists over just a few mm or over the whole dish. The response of the cells in the confluent center of the ring is to reduce growth and increase procollagen expression, unaltered by the large medium volume. As previously shown with procollagen production, all that matters is the 2-dimensional cell density over a distance of about 1 mm.

Shaking converts the effective environment into a 3-dimensional space. The observation that shaking the medium does not alter the effect of the CDS if enough cells are present ($5 \times 10^5$/ml compared to $5 \times 10^3$/ml), indicates that the medium can be saturated with the CDS to the point where the frequency of reassociation of CDS with the cell layer prevents dilution of the biological effect.

Example 6
Biological Activity of the CDS Released into the Medium

Based solely on the results presented in Example 5, it might be expected that the biological activity of CDS is an inhibitor of PAT cell proliferation and a promoter of procollagen gene expression. However, the biological activity of CDS recovered from the medium of agitated PAT cells was growth stimulatory.

Confluent cultures of PAT cells were agitated in the minimum amount of medium that would cover the dish (1 ml), thereby releasing CDS into the medium. This medium was applied to cells initially seeded in cloning rings. Then 5 ml of this conditioned medium was used on the test cells. This gave about a 500 fold increase in the amount of CDS available to each cell. The test cells were grown for 5 days before conditioned medium was added, and then two days with it. PAT cells receiving the conditioned medium were not inhibited from growing, but rather, they were dramatically stimulated to divide. At higher concentrations, even the cells that were at a confluent density could be induced to divide (see below). In contrast the control plates showed large amounts of cell death at the edge of the circle of cells.

Thus, in the case of a uniformly confluent culture, shaking releases a factor which is stimulatory for the proliferation of a homologous culture, but the presence of the factor in the original culture inhibits growth.

One could postulate that the inhibitor of growth is still in the cell layer counteracting the effect of the growth stimulator. This, however, is not consistent with results obtained from shaking the medium over an "island" of cells in the middle of the dish, e.g. where there is a large medium-to-cell ratio. In this case, agitation of the medium caused the cells to grow.

Instead, these experiments support the concept that the biological activity of CDS in the cell layer can be different from the CDS activity observed in the medium. The mechanism by which the biological activity of CDS in the cell layer changes as the cell density increases is unknown at the present time.

Example 7
Physical Characteristics of CDS

CDS activity as a growth stimulator was used to assay its presence and allowed its characterization and purification. CDS was found to be stable to ammonium sulfate precipitation and this enabled it to be concentrated >100-fold. At this concentration a small amount was tested under various conditions and then diluted into medium to test the retention of activity at a 1×concentration.

CDS retained at least 75% of its biological activity after exposure to low pH (50 mM sodium acetate, pH 5.2 for 60 minutes), disulfide bond reduction (10 mM DTT, for 30 minutes) and heat (90° C. for 10 minutes). It was also stable in medium or PBS for months at 4° C. On the other hand, exposure to Tris ion (50mM Tris pH 7.5 for 60 minutes) resulted in the loss of greater than 90% of CDS biological activity, while Tris base (50 mM Tris pH 8.8 for 60 minutes) had little effect (retention of greater than 90% biological activity).

Example 8
Proteolytic Sensitivity of CDS

The CDS was tested for sensitivity to proteolytic digestion with proteinase K (P9290-Sigma) and pronase (P4531)—Sigma) and trypsin (T-8386-Sigma). Binding the enzyme to agarose or acrylamide was used to facilitate removal of the enzyme after the reaction. The bound enzyme (1 unit) was washed 2× in basal medium (30 min, on a rocking platform). Then medium containing 1×CDS was treated for 2 hours at 39° C. with rocking, spun in a table top centrifuge and filter sterilized. Basal medium was treated similarly and used as a control. Serum and ascorbate was then added to each sample and the CDS so treated was then tested for activity as described above.

The CDS molecule was insensitive to trypsin (greater than 75% of biological activity retained) but was sensitive to both protease enzymes (less than 10% of biological activity retained). Protease digestion of CDS also resulted in a toxic response to all the cells tested. A similar toxicity developed in CDS samples that were repeatedly freeze thawed.

Example 9
Purification of CDS

Since the CDS is stable when subjected to several treatments that disrupt aggregation, these treatments (heat, pH, and DTT treatment) were tested to determine whether they altered the chromatographic properties of CDS on a Bio-Gel P-30 column.

Only DTT addition had a significant effect. After treatment, most of the CDS activity was eluted, not in the flow through, but in the fractions just following the void volume peak, showing some penetration of CDS into the pores of the gel (FIG. 1). In FIG. 1, continuous arrows denote fractions containing CDS activity prior to DTT treatment and the dashed arrows denote fractions containing CDS activity after DTT treatment. This demonstrated that the active component of CDS is a molecule in the range of 25–35 kD which is found in an aggregated, possibly multimeric, form in the medium of agitated cell cultures. After treatment with DTT, the monomeric 25–35 kD molecule retains CDS activity. This information was used to develop a purification protocol. The medium from agitated cultures was concentrated by ammonium sulfate precipitation (this step was skipped where the volumes were small, for example, recovery of radioactively labeled CDS) and the concentrate was ultrafiltered using a 30 kD exclusion membrane. All the activity was retained in the >30 kD fraction. Then, the retentate was treated with 10 mMDTT for 30 minutes and again ultrafiltered using a 30 kD membrane. About half of the activity now passed through the filter. The activity from the flowthrough (the equivalent of 50 ml of conditioned medium) showed no bands on SDS-PAGE after silver staining. Yet, this material retained its biological activity.

Figure 2:
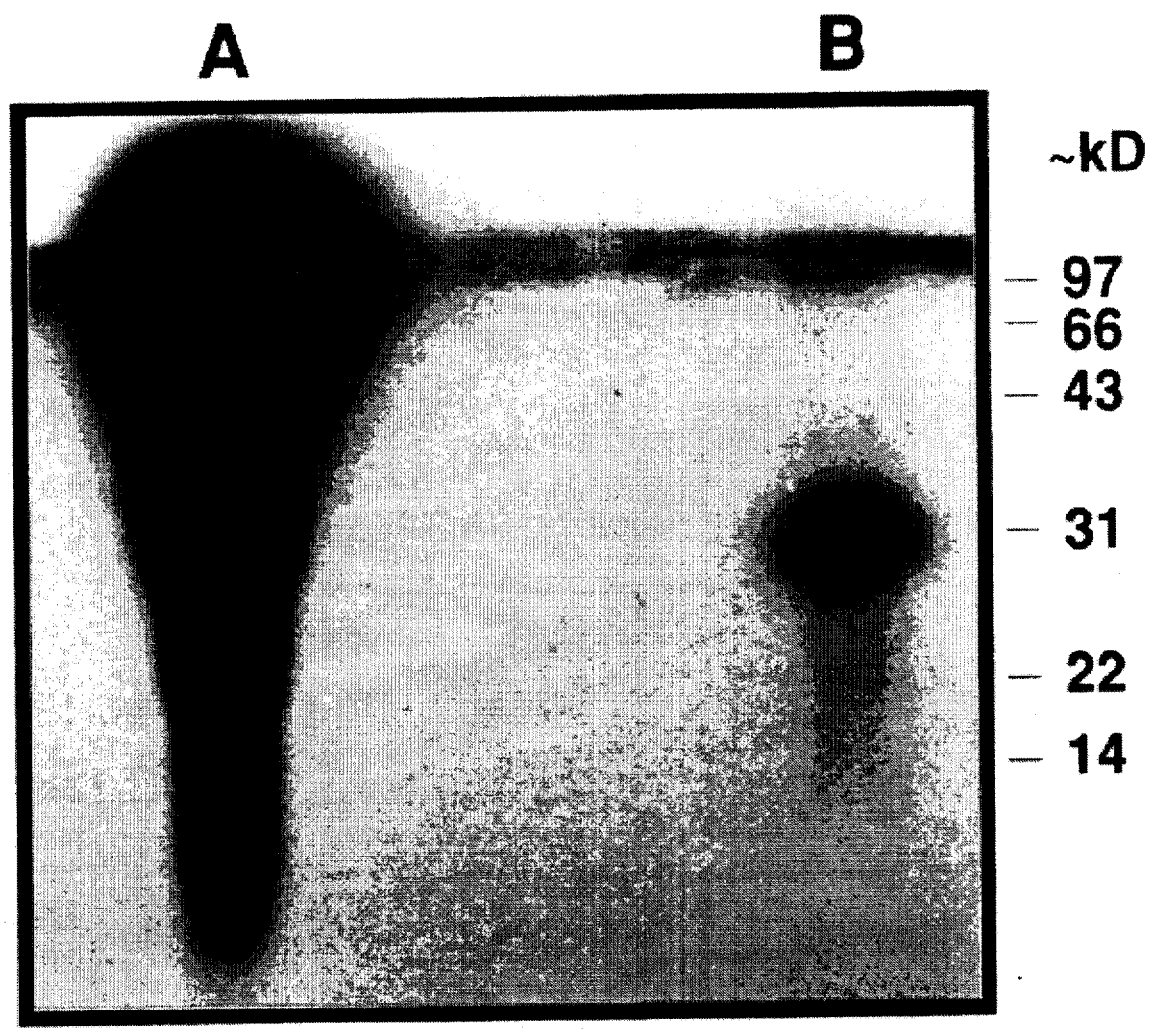
FIG. 2 is a radiographic imaging of an SDS-PAGE of the high and low molecular weight fraction of cells labeled for 12 hours with radioactive amino acids. Lane A is the >30 kD fraction after DTT treatment and lane B is the <30 kD fraction. The gel was exposed to radiosensitive film for 1 month, thereby demonstrating that no other labelled bands were present in lane B.

When the conditioned medium was used from cells labeled overnight with high levels of radiolabeled amino acids, subjected to the same fractionation procedure above, run on SDS-PAGE, and fluorographed, a single diffuse band was observed, with an apparent molecular weight of approximately 30 kD (FIG. 2). In FIG. 2, the left lane was loaded with the retentate of a DTT treated 30 kD ultrafiltration procedure and the right lane was loaded with the flowthrough.

What is claimed is:

1. A method of producing substantially purified proteinaceous CDS capable of initially stimulating the proliferation of embryonic tendon cells in culture and thereafter promoting differentiated procollagen gene expression, comprising:

A. providing primary tendon cells in confluent cell cultures,

B. providing conditions, including an unsupplemented medium, in which the cells secrete polypeptides which include CDS, C. agitating the culture to increase the amount of CDS in the medium, D. collecting CDS-containing unsupplemented medium, and E. recovering and purifying the CDS from the collected CDS-containing unsupplemented medium.

2. The method of claim 1 wherein said recovering and purifying is accomplished by:

a) first ultrafiltering said CDS-ocontaining medium with a 30 kD ultrafilter to yield a retentate containing CDS biological activity in a molecular complex such that said complex has an apparent molecular size greater than 30 kD;

b) denaturing the retentate of step "a" with a sufhydryl bond-disrupting agent thereby disrupting said complex to yield CDS as a free protein, said CDS having a molecular size of about 30 kD;

c) second ultrafiltering the product of step "b" with a 30 kD ultrafilter; and d) collecting the filtrate which contains purified CDS.

3. The method of claim 1 in which the cells are derived from embryonic chicken tendons.

\* \* \* \* \*